(12) United States Patent
Henderson

(10) Patent No.: US 6,471,643 B1
(45) Date of Patent: Oct. 29, 2002

(54) LARYNGOSCOPE

(75) Inventor: John J. Henderson, Glasgow (GB)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/544,481

(22) Filed: Apr. 7, 2000

Related U.S. Application Data

(63) Continuation of application No. PCT/US98/06438, filed on Oct. 12, 1998.

(30) Foreign Application Priority Data

Oct. 11, 1997 (GB) .............................................. 9721533
Jun. 17, 1998 (GB) .............................................. 9812973

(51) Int. Cl.$^7$ ............................................. A61B 1/267
(52) U.S. Cl. ........................ 600/185; 600/190; 600/194
(58) Field of Search ................................ 600/190, 194, 600/185

(56) References Cited

U.S. PATENT DOCUMENTS

| | | | |
|---|---|---|---|
| 3,856,001 A | | 12/1974 | Phillips |
| 4,112,933 A | * | 9/1978 | Moses ......................... 600/190 |
| 4,126,127 A | * | 11/1978 | May ........................... 600/187 |
| 4,295,465 A | * | 10/1981 | Racz et al. .................. 600/192 |
| 4,360,008 A | * | 11/1982 | Corazzelli, Jr. ............. 600/194 |
| 4,527,553 A | | 7/1985 | Upsher |
| 4,827,910 A | * | 5/1989 | Mathews, III ............... 600/194 |
| 5,063,907 A | * | 11/1991 | Musicant et al. ........... 600/186 |
| 5,065,738 A | * | 11/1991 | Van Dam .................... 600/185 |
| 5,184,603 A | * | 2/1993 | Stone .......................... 600/193 |
| 5,263,472 A | | 11/1993 | Ough |
| 5,287,848 A | * | 2/1994 | Cubb et al. ............. 128/200.26 |
| 5,571,071 A | * | 11/1996 | Shapiro ....................... 600/187 |
| 5,984,863 A | * | 11/1999 | Ansari ......................... 600/185 |
| 5,993,383 A | * | 11/1999 | Haase .......................... 600/191 |

FOREIGN PATENT DOCUMENTS

| | | |
|---|---|---|
| DE | 32 17 476 A1 | 9/1993 |
| EP | 0 194 588 A1 | 6/1986 |

* cited by examiner

Primary Examiner—Michael Peffley
Assistant Examiner—Jocelyn Ram
(74) Attorney, Agent, or Firm—St. Onge Steward Johnston & Reens LLC

(57) ABSTRACT

A laryngoscope, especially for introducing a tube into the trachea, comprises a laryngoscope spatula of substantially straight shape and a handle. The laryngoscope spatula is configured, at least in part, as a tubular hollow body, with a longitudinal opening, extending from a proximal end to a distal end of the laryngoscope spatula, formed laterally in the laryngoscope spatula.

18 Claims, 3 Drawing Sheets

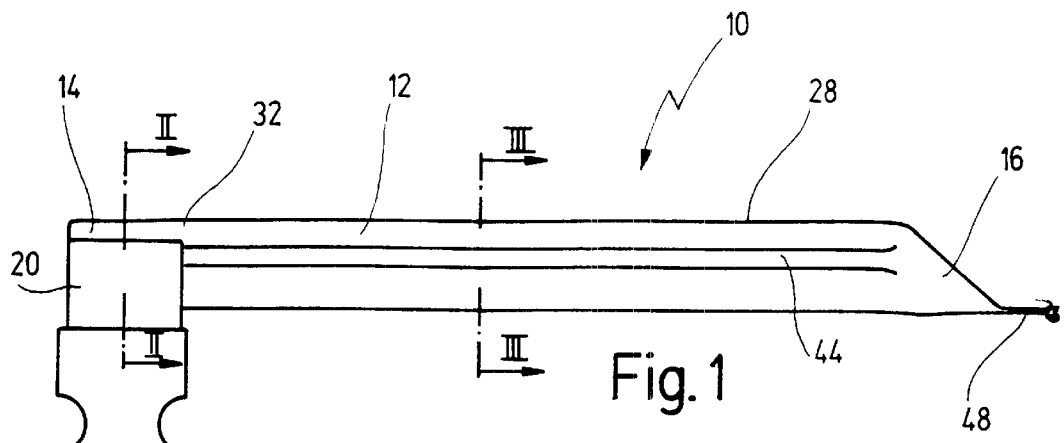
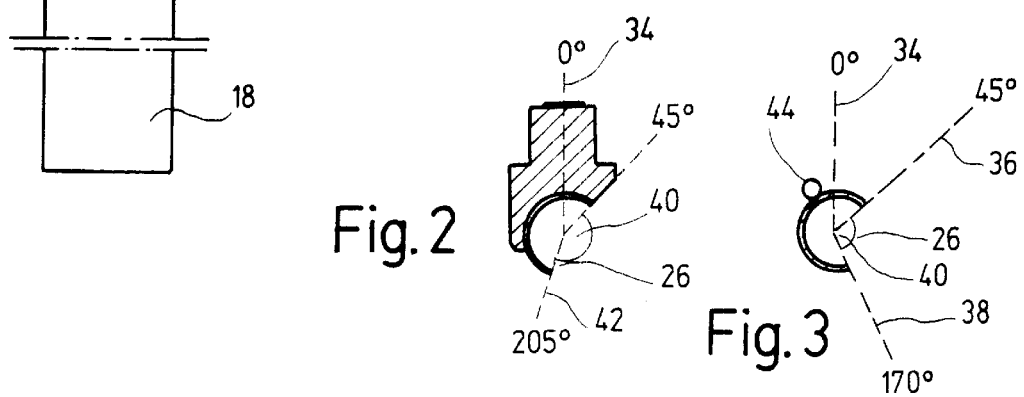
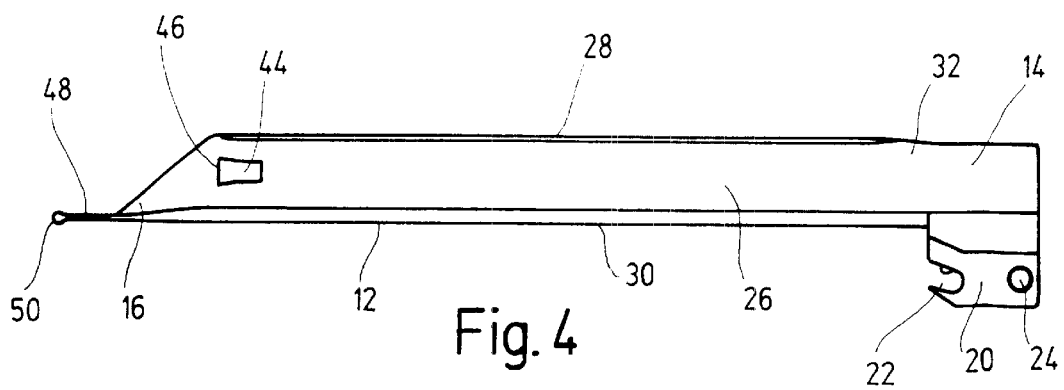
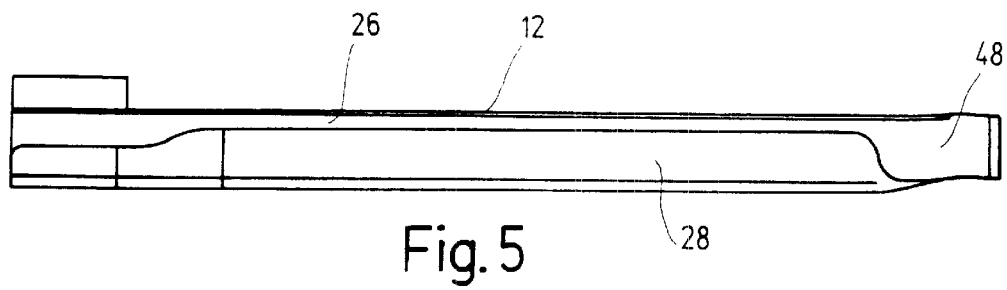

LARYNGOSCOPE

CROSS-REFERENCE TO PENDING APPLICATION

This application is a continuation of pending International Application PCT/EP98/06438.

BACKGROUND OF THE INVENTION

The present invention relates to a laryngoscope, especially for introducing a tube into the trachea, having a laryngoscope spatula of substantially straight shape and a handle.

A laryngoscope of this kind is generally known.

A laryngoscope is a medical instrument that serves to visually observe the larynx. In anesthesia, such a laryngoscope is simultaneously used for introducing a tube, for example an anesthetic tube, with the aid of the laryngoscope into the patient's trachea under visual control in order to be able to supply the patient with air during anesthesia. The process of introducing a tube into the trachea can be considerably simplified by a laryngoscope.

A laryngoscope was described for the first time in 1895, and was used for the first time for intubation of a patient under visual control in 1912. Since then, the use of laryngoscopes for tracheal intubation under visual control has become an essential practical part of anesthesia and in intensive medical treatment.

Up to 1943, laryngoscopes with straight laryngoscope spatulas were in use. It was the first time in 1943 that Mackintosh described a laryngoscope with a curved laryngoscope spatula, which was used in laryngoscopy in combination with a novel application technique. Since then, the use of the curved laryngoscope has established itself as standard process, because the method after Mackintosh is easier to apply with an average patient than a method using a laryngoscope with straight laryngoscope spatula. Another reason is seen in the fact that many anesthetists did not arrive at the optimum method with a straight laryngoscope since they introduced the laryngoscope through the mouth centrally, over the back of the tongue. This method formerly used is little successful with most of the more difficult patients.

In contrast, the method after Mackintosh has proved to be very successful. Unfortunately, however, it does not allow visual observation of the larynx with 2% to 5% of all patients. With these patients, tracheal intubation can be achieved by a "blind" process without visual control. However, blind processes are connected with a plurality of risks, including the risk of a major trauma of tissue involved.

Problems encountered in connection with tracheal intubation are a main reason for fatalities under anesthesia. One has estimated that in the western world 600 fatalities annually occur as a result of problems encountered during tracheal intubation. In addition, other major complications, such as damage to the brain, the trachea, the esophagus and other tissue, may lead to fatalities.

Although there are a number of possibilities to overcome the difficulties connected with intubation, all blind methods are connected with significant fault rates. The ideal method should be relatively simple, make use of simple equipment and provide a high rate of success, and a low fault rate.

An optimally suited method (paraglossal straight laryngoscopy) of tracheal intubation for these patients has been described by the inventor of the present invention in 1997. The method described provides a high rate of success where the method after Mackintosh fails. Unfortunately, however, no laryngoscope is available at present that can be used for that method without any disadvantages.

Two problems are encountered in difficult tracheal intubation: The first problem consists in the necessity to observe the larynx, the second in the necessity to introduce the tube through the larynx and into the trachea.

The straight laryngoscope used most frequently is the laryngoscope after Miller. When this laryngoscope is used for the paraglossal method, it is usually successful where the method after Mackintosh fails. However, manipulation of the tube to be introduced requires that an additional space be opened along the tube. This in turn requires an increased lifting pressure. Such increased lifting force cannot always be achieved, and may in addition have a traumatic effect. In addition, the configuration of the laryngoscope as such also impairs the manipulation of the tube to be introduced.

There have been known further laryngoscopes (for example after Kleinsasser, Holinger, Benjamin) which permit good visual observation of the larynx with difficult patients. However, in these cases introduction of the tube is complicated and requires a plurality of steps and much time, which may be critical with difficult patients.

Another known laryngoscope, the PCV laryngoscope, permits easy introduction of the tube. Unfortunately, however, this laryngoscope does not present an optimum configuration. It comprises a curvature which on the one hand facilitates the introduction of the laryngoscope, while making visual inspection of the larynx unsatisfactory with most of the difficult patients. In addition, the configuration of the tip impairs the desired best possible control of the epiglottis. The light carrier projects into the lower side of the laryngoscope, where tissue pressure is exerted by the laryngoscope spatula, whereby the risk of a tissue trauma is increased. In addition, the PVC laryngoscope is cost-intensive.

As has been mentioned before, the laryngoscope after Mackintosh, used most frequently, is curved along its lengthwise axis. However, it is realized more and more that such configuration is connected with a higher fault rate in tracheal intubation than is the case with laryngoscopes with straight laryngoscope spatulas.

It is, therefore, the object of the present invention to improve a laryngoscope of the before-mentioned kind in such a way that the laryngoscope will permit improved visual control of the larynx and, at the same time, improved introduction of the tube through the larynx and into the trachea.

SUMMARY OF THE INVENTION

According to the present invention, this object is achieved by a laryngoscope, in particular for introducing a tube into a trachea of a patient, comprising:

a handle; and a laryngoscope spatula connected to said handle, said laryngoscope spatula having a longitudinally substantially straight shape, and, further being configured, at least in part, as a tubular hollow body having a proximal end and a distal end, wherein said tubular hollow body comprises a lateral longitudinal opening extending from said distal end to said proximal end, and, wherein said laryngoscope spatula comprises at its distal end a substantially flat tip adjacent to said distal end which is in transverse direction substantially straight.

Compared with the known laryngoscopes, the tubular configuration of the laryngoscope spatula according to the invention provides the advantage that insertion of a tube into the trachea with the aid of a laryngoscope is considerably simplified. The tube can be introduced, according to a basic method, either directly through the lumen of the laryngoscope spatula or indirectly under visual control, using an introduction aid, likewise through the lumen of the laryngoscope spatula. Unlike the known laryngoscopes, it is not necessary with this way of introducing the tube, rendered possibly by the tubular configuration of the laryngoscope spatula, to open a free space on the side of the laryngoscope, whereby the lifting force required is reduced. Consequently, the tube can be introduced less traumatically and with success even with difficult patients. The laryngoscope spatula is, however, not configured as a fully closed tubular hollow body, but is provided with a longitudinal opening in its lengthwise direction. The laryngoscope spatula according to the present invention therefore can be described as a slotted tube. The lateral longitudinal opening leads to further considerable advantages of the invention. On the one hand, the lateral longitudinal opening permits improved visual observation of the area of the larynx during introduction of the tube. The longitudinal opening enlarges the field of vision so that binocular observation is rendered possible. On the other hand, the lateral longitudinal opening also facilitates removal of the laryngoscope after the tube has been inserted, as the laryngoscope spatula can be stripped off laterally from the tube. In addition, the lateral longitudinal opening also permits introduction of the tube into the laryngoscope spatula sized in the circumferential direction. In combination with the straight design of the laryngoscope spatula, optimum observation of the larynx is achieved even with difficult patients.

By means of the flat tip at the distal end, the laryngoscope spatula is not tubular, but rather flat at its distal end. This is of advantage on the one hand for achieving optimum control of the epiglottis. On the other hand, the field of vision for visual observation, especially for visual observation of the larynx, is further increased, and visual control of the introduction of the tube is improved. This feature also leads to improve control of the epiglottis, in that the laryngoscope spatula transitions from a tubular cross-section to a plate-like cross-section in its distal area.

In a preferred embodiment of the invention, the laryngoscope spatula is approximately circular in cross-section.

It is an advantage of this configuration that the tube, which is to be introduced into the trachea and which usually is circular in cross-section, can be guided with more ease in the laryngoscope spatula.

According to further preferred embodiment, the cross-section of the laryngoscope spatula tapers in a proximal area of the tubular hollow body.

Given the fact that the laryngoscope spatula is introduced into the patient's mouth, where the proximal area comes to lie between the patient's teeth, this provides the advantage to reduce the risk of damage to the teeth. The tapering configuration of the proximal area of the laryngoscope spatula reduces the contact between the laryngoscope spatula and the teeth when lifting or lowering the laryngoscope spatula.

According to a further preferred embodiment, the lateral longitudinal opening of said tubular hollow body widens toward the proximal end of said tubular hollow body.

This feature provides the advantage that the tube can be introduced into the lumen of the laryngoscope spatula with more ease. In addition, the enlargement of the longitudinal opening also facilitates the action of stripping-off the laryngoscope from the tube once the tube has been introduced into the trachea.

According to a further preferred embodiment, the lateral longitudinal opening has an opening angle, viewed in cross-section, in the range of approximately 180° to approximately 90°.

Within this angular range of the opening angle of the longitudinal opening, viewed in cross-section, the tube to be introduced can on the one hand be safely introduced into the laryngoscope spatula and guided, while on the other hand the longitudinal opening permits an increased field of vision and facilitates the removal of the laryngoscope spatula from the tube after insertion of the tube into the trachea.

It is further preferred if the tip is in longitudinal direction slightly curved or straight.

According to a further preferred embodiment, the point extends approximately over the whole width of the laryngoscope spatula.

This feature provides the advantage that the tip is a planar extension so that the risk of a tissue trauma in the area of the larynx is further reduced.

According to a further preferred embodiment, the tip exhibits a bead-like thicker portion.

This feature provides the advantage that the risk of damage to soft tissue is further reduced.

According to a further preferred embodiment, a light pipe, whose output end opens into the lumen of the laryngoscope spatula, is guided along the laryngoscope spatula.

Accordingly, the light pipe, consisting for example of a fiber bundle received in a small tube, is guided in this embodiment from the proximal end of the laryngoscope spatula to the distal end of the laryngoscope spatula, and the light-emitting end of the light pipe ends at the distal end of the laryngoscope spatula in the lumen of the laryngoscope spatula, whereby illumination of the field of observation in the area of the larynx is advantageously further improved since the propagation of light is not obstructed by tissue, especially soft tissue, in contact with the laryngoscope spatula. The light emitting end of the light pipe is directed in such a way that optimum illumination of the larynx is achieved.

According to a further preferred embodiment, the proximal end of the laryngoscope spatula comprises a mounting section for locking the handle on the laryngoscope spatula.

This provides the advantage that the laryngoscope spatula can be designed as disposable unit, while the handle, containing the light source, can be reused. However, it is also possible to design the laryngoscope spatula in such a way that it can be mounted undetachably together with the handle. Standard handles comprising a fiberoptic system can be used. When using a standard handle, the laryngoscope according to the invention can be produced at low cost.

According to a further preferred embodiment, the lumen of the laryngoscope spatula is adapted to the diameter of the tube to be introduced.

This provides the advantage that the laryngoscope according to the invention is always adapted to the particular tube size. It is then possible to have available different laryngoscopes of differently sized cross-section of the laryngoscope spatula in order to always have available the optimum laryngoscope for the respective application.

According to a further preferred embodiment, an insufflation channel, ending at the distal end of the laryngoscope spatula, is arranged on the laryngoscope spatula.

This insufflation channel may, advantageously, be used to insufflate oxygen, for example an intermittent oxygen jet at high pressure, so that emergency respiration can be carried out if the introduction of the tube should be delayed. The insufflation channel may also be used to administer local anesthetics to the larynx and other organs in the patient's respiratory tract.

Further advantages will become apparent from the description that follows, and the attached drawing.

It is understood that the features mentioned above and those yet to be explained below can be used not only in the respective combinations indicated, but also in other combinations or in isolation, without leaving the context of the present invention.

BRIEF DESCRIPTION OF THE DRAWINGS

The invention will be described in more detail and explained below with reference to certain exemplifying embodiments and the attached drawings. In the drawings:

FIG. 1 shows a side view of a laryngoscope according to a first embodiment of the invention, viewed from the right closed side of the laryngoscope spatula;

FIG. 2 shows a section through the laryngoscope according to FIG. 1, taken along line II—II, with the handle removed;

FIG. 3 shows a section through the laryngoscope according to FIG. 1, taken along line III—III;

FIG. 4 shows a side view of the left open side of the laryngoscope according to FIG. 1;

FIG. 5 shows a bottom view of the laryngoscope according to FIG. 1;

DETAILED DESCRIPTION OF PREFERRED EMBODIMENTS

Figure 6:
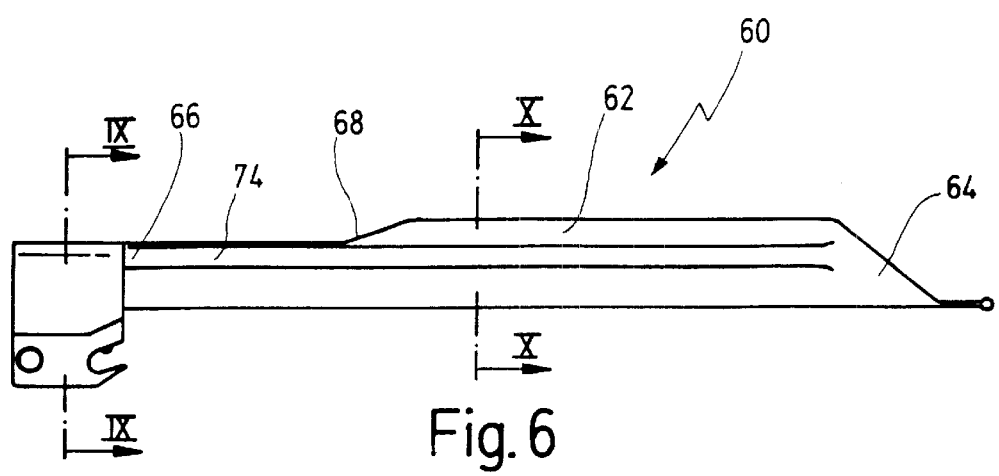
FIG. 6 shows a side view of the right side of the laryngoscope according to a further embodiment, without the handle.
Figure 7:
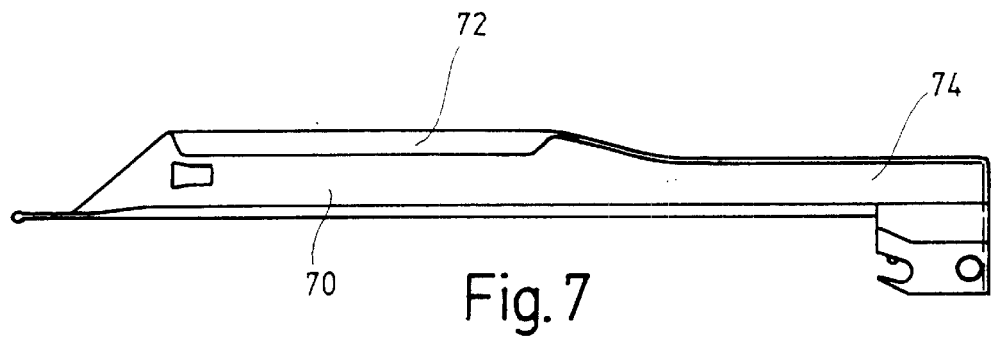
FIG. 7 shows a side view of the left side of the laryngoscope according to FIG. 6.
Figure 8:
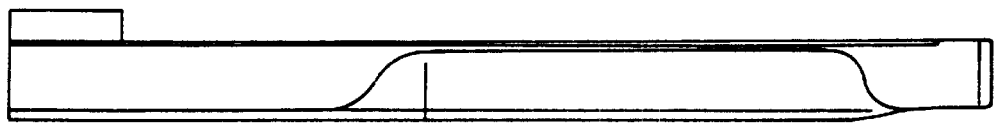
FIG. 8 shows a bottom view of the laryngoscope according to FIG. 6.
Figure 9:
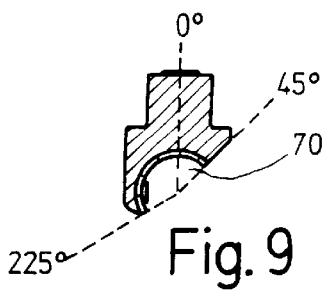
FIG. 9 shows a section taken along line IX—IX in FIG. 6.
Figure 10:
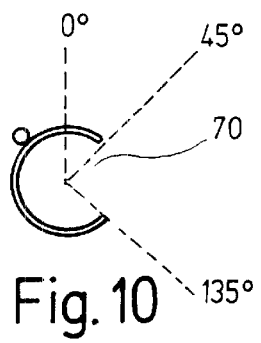
FIG. 10 shows a section taken along line X—X in FIG. 6.

FIGS. 1 to 5 show a laryngoscope indicated generally by reference numeral 10. The laryngoscope 10 is introduced into the area of a patient's mouth and pharyngeal cavity, as an inspection instrument for inspecting the larynx. For anesthetic purposes, the laryngoscope 10 further serves for introducing a tube by means of the laryngoscope 10 into a patient's trachea under visual control in order to permit the patient to be artificially respirated through the tube under anesthesia.

The laryngoscope 10 comprises a laryngoscope spatula 12; the laryngoscope spatula 12 has a proximal end 14 and a distal end 16.

Connected to the proximal end 14 of the laryngoscope spatula 12 is a handle 18 projecting approximately at a right angle from the laryngoscope spatula 12.

The handle 18 can be detached from the laryngoscope spatula 12. To this end, a mounting section is arranged at the proximal end 14 of the laryngoscope spatula 12, which permits the handle 18 to be locked on the laryngoscope spatula 12. The mounting section 20 comprises a recess 22 of oblong shape, into which a transverse pin of a handle 18 (not shown) can be inserted. The proximal end of the mounting section 20 carries a locking element 24 in the form of a ball biased outwardly by means of a spring, for engaging into a corresponding cup-shaped recess in the handle 18. For mounting the handle 18 on the laryngoscope spatula 12, one initially inserts the pin into the recess 22 and then pivots the handle to the rear so that the locking element 24 snaps into the handle 18.

Instead of providing a detachable handle 18 it is, however, also possible to make the handle undetachable and fixed on the laryngoscope spatula 12.

The laryngoscope spatula is substantially straight, as appears from a comparison of the representations of FIG. 1 and FIG. 5.

Further, the laryngoscope spatula 12 is designed as a tubular hollow body. As appears from FIG. 4, the laryngoscope spatula 12 comprises a lateral longitudinal opening 26 extending from its proximal end 14 to its distal end 16. The longitudinal opening 26 is limited in the circumferential direction of the laryngoscope spatula 12. A lower side 28 (compare FIG. 5), also known as oropharyngeal side, is closed, as is an upper side 30 (epiglottal side) of the laryngoscope spatula 12. Thus, the longitudinal opening 26 extends on one side, i.e. on the left side of the laryngoscope spatula 12. The representation of FIG. 1, therefore, shows the closed right side of the laryngoscope spatula 12, while FIG. 4 shows the open side, i.e. the view into the longitudinal opening 26.

The laryngoscope spatula 12 is circular in cross-section, as is shown in FIGS. 2 and 3.

The cross-section of the laryngoscope spatula 12 tapers slightly in a proximal area 32.

The longitudinal opening 26 widens toward the proximal end 14. Widening of the longitudinal opening 26 occurs in the proximal area 32. This is shown in more detail in FIGS. 2 and 3.

FIG. 3 shows a section taken along line III—III in FIG. 1, i.e. a section through the laryngoscope spatula 12 in an area distal from the proximal section 32. In the circumferential direction, the laryngoscope spatula 12 extends over an angle of approximately 45° in clockwise direction to an axis 36, relative to a vertical axis 34 (0° axis). The longitudinal opening 26 extends from the axis 36 to a further axis 38 (170° axis), over an opening angle 40 of approximately 125°.

At the proximal end 14, the longitudinal opening 26 extends, however, from the 45° axis to an axis 42 (205° axis) so that at the proximal end 14 the opening angle 40 of the longitudinal opening 26 covers approximately 160°.

Starting out from the handle 18, a light pipe 44 is guided along the outside of the closed right side of the laryngoscope spatula 12, from its proximal end 14 to its distal end 16. At the distal end 16, the light pipe 44 enters the lumen of the laryngoscope spatula 12 so that a light-emitting end 46 of the light pipe 44 is arranged on the inside, i.e. in the lumen of the laryngoscope spatula 12. The light pipe 44 comprises a fiberoptic bundle which is guided in a small tube.

In cases where a flat light pipe is used, the light pipe 44 may also be guided on the inside of the laryngoscope spatula 12, from the proximal end 14 to the distal end 16, because in this case the light pipe 44 will not present any obstruction when pushing the tube through the lumen, i.e. the inner cavity of the laryngoscope spatula 12.

At the distal end 16, the laryngoscope spatula 12 tapers to form a flat tip 48. As can be seen in FIG. 5, the tip 48 extends over the entire width of the laryngoscope spatula 12. A distal end of the tip 48 exhibits a bead-like thicker portion 50. The thicker portion 50 extends approximately at a right angle to the longitudinal direction of the laryngoscope spatula 12.

At its distal end 16, the laryngoscope spatula 12 therefore transitions from a circular cross-sectional shape to a substantially flat planar shape, the tip 48 forming, in the embodiment illustrated in FIGS. 1 to 5, a substantially straight extension of the upside 30 of the laryngoscope spatula 12.

FIGS. 6 to 10 show a further embodiment of a laryngoscope 60. Here again, the laryngoscope 60 comprises a laryngoscope spatula 62 of substantially straight configuration as in the embodiment illustrated in FIGS. 1 to 5.

The laryngoscope spatula 62 is formed as a tubular hollow body, again of circular cross-section. Starting out from a distal end 64, the cross-section of the laryngoscope spatula 62 tapers toward a proximal end 66, but unlike the embodiment shown in FIGS. 1 to 5, the reduction in cross-section is stronger in a transitional area 68 between the distal end 64 and the proximal end 66 than in the case of the embodiment described first. The reduction in cross-section in the transitional area 68 is gradual so that the laryngoscope spatula 62 is free from any edges that might have a traumatic effect. Unlike the embodiment described first, the proximal area of reduced cross-section of the laryngoscope spatula 62 moreover has a greater length.

A further difference, relative to the embodiment illustrated in FIGS. 1 to 5 relates to the longitudinal opening 70 formed in the laryngoscope spatula 62 between the distal end 64 and the proximal end 66. In contrast to the embodiment described above with reference to FIGS. 1 to 5, the longitudinal opening 70 extends, in the distal area 72, from the 45° axis to a 135° axis in the circumferential direction, covering an opening angle of approximately 90°. This means that the longitudinal opening 70 is narrower in circumferential direction with this embodiment, compared with the longitudinal opening 26 of the laryngoscope spatula 12. In a proximal area 74 the opening 70 widens in circumferential direction to a 225° axis (compare FIG. 9) relative to the distal area 72. Consequently, the opening angle of the longitudinal opening 70 is approximately 180° in the proximal area and, thus, larger than in the corresponding section of the laryngoscope spatula 12.

The laryngoscope 10 according to FIGS. 1 to 5 and the laryngoscope 60 according to FIGS. 6 to 10 serve to introduce a tube through the lumen of the laryngoscope spatula 12 or 62, respectively, into a patient's trachea. Introducing a tube into the lumen of the laryngoscope spatulas 12 or 62 can, as a standard method, be effected from the proximal end through the lumen of the laryngoscope spatula 12 or 62, or with the aid of a boogie, and this in each case under visual control through the larynx and into the trachea.

In addition to these two standard methods, where the laryngoscope is introduced on the right side of a patient's mouth, the laryngoscope spatula 62, having a smaller longitudinal opening 70 than the embodiment according to FIGS. 1 to 5, makes it easier to carry out the two before-mentioned methods also on the left side of a patient's tongue.

In addition to the two standard methods, the laryngoscope spatula 12 according to FIGS. 1 to 5, with the larger longitudinal opening 26, permits a tube to be introduced under visual control laterally from the open side of the lumen of the laryngoscope spatula 12.

Depending on the particular patient it may be advisable to use either the laryngoscope 10 according to FIGS. 1 to 5, or the laryngoscope 60 according to FIGS. 6 to 10.

Figure 11:
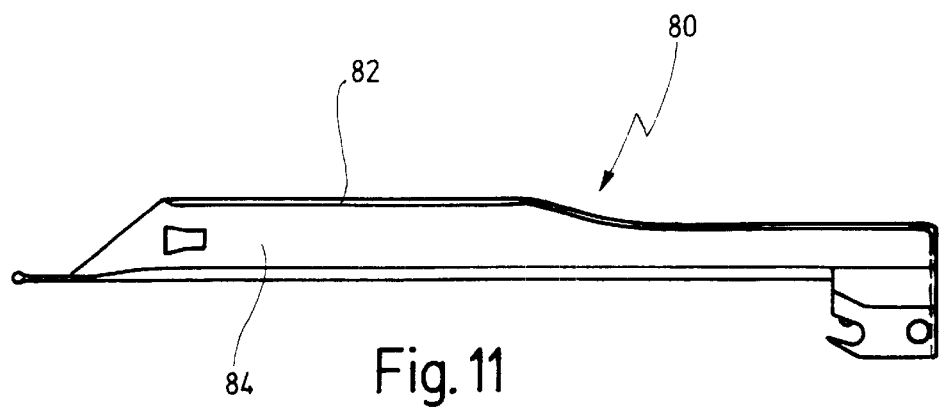
FIG. 11 shows a side view of a laryngoscope according to a further embodiment, corresponding to FIGS. 4 and 7.

FIG. 11 shows a further embodiment of a laryngoscope 80. The laryngoscope 80 comprises a laryngoscope spatula 82, the geometry of which is a combination of the laryngoscope spatulas 12 and 62. The laryngoscope spatula 62 and the laryngoscope spatula 82 have in common that the cross-section reduces more rapidly toward the proximal end and that the proximal area of smaller cross-section is long. The laryngoscope spatula 82 has in common with the laryngoscope spatula 12 that a longitudinal opening 84 in the laryngoscope spatula 82 has a generally large opening angle in the distal area.

Figure 12:
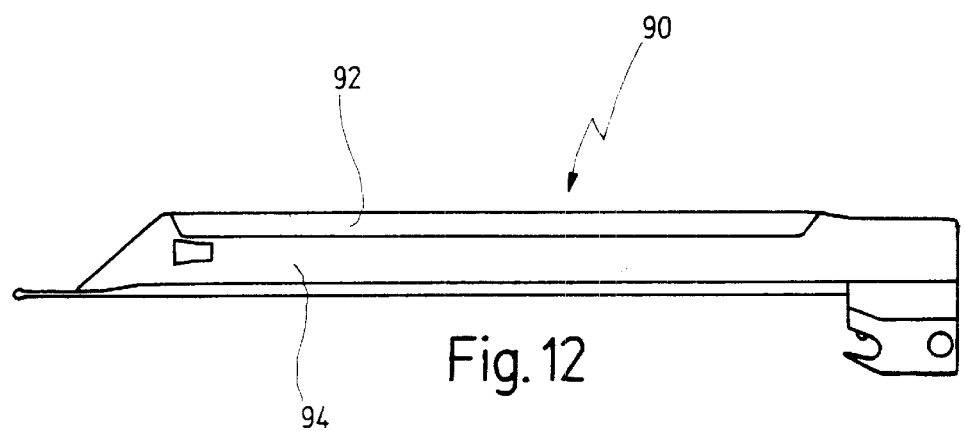
FIG. 12 shows a side view of a still further embodiment of a laryngoscope, corresponding to FIGS. 4, 7 and 11.

FIG. 12 shows a still further embodiment of a laryngoscope 90 comprising a laryngoscope spatula 92 which again is provided with a longitudinal opening 94. The geometry of the laryngoscope spatula 12 again is a combination of the geometry of the laryngoscope spatula 12 according to FIGS. 1 to 5 and of the laryngoscope spatula 62 according to FIGS. 6 to 10. But unlike the embodiment according to FIG. 11, the longitudinal opening 64 in the distal area is smaller in this case as with the embodiment according to FIGS. 6 to 10, whereas the reduction in cross-section of the laryngoscope spatula 92 is less pronounced lo toward the proximal end, similar to the embodiment according to FIGS. 1 to 5.

Figure 13:
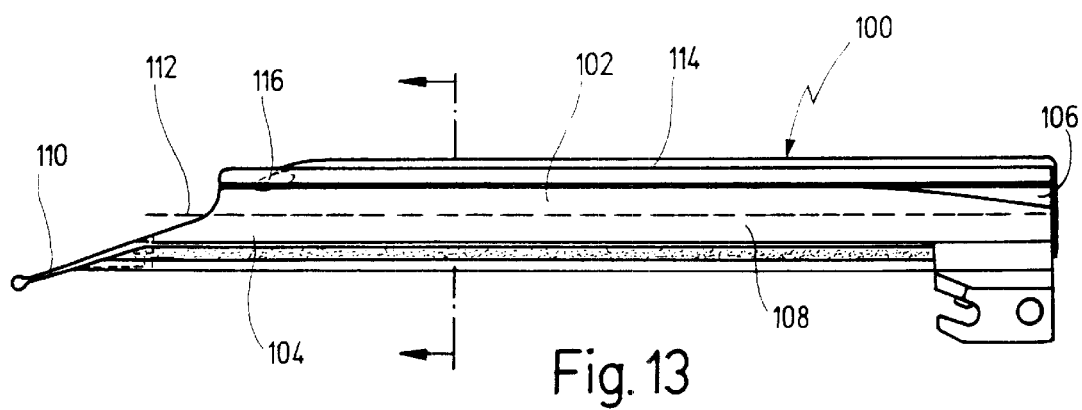
FIG. 13 shows a side view of a laryngoscope according to a still further embodiment, corresponding to FIGS. 11 and 12.
Figure 14:
FIG. 14 shows a section through the laryngoscope according to FIG. 13, taken along line XIV—XIV.

FIGS. 13 and 14 finally show a last embodiment of a laryngoscope 100. The laryngoscope 100 comprises a laryngoscope spatula 102, again provided with a longitudinal opening 108 extending from a distal end 104 to a proximal end 106.

But unlike the previous embodiments, the laryngoscope spatula 102 tapers at its distal end to 104 to form a flat, planar tip 110 extending obliquely to a longitudinal axis 112 of the laryngoscope spatula 102. Instead of the straight design of the tip illustrated in all embodiments, the tip may also be curved.

Further, an insufflation channel 114 is arranged on the outside of the laryngoscope spatula 102. The insufflation channel 114 comprises an outlet 116 in the area of the distal end 104 of the laryngoscope spatula 102. Through the insufflation channel 114, oxygen can be supplied to the patient intermittently and at high pressure in case emergency respiration of the patient should become necessary. Preferably, such an insufflation channel may also be provided with the embodiments described before.

In all illustrated embodiments, the laryngoscope spatulas 12, 62, 82, 92 and 102 exhibit a narrow shape so as to facilitate the process of positioning the laryngoscope spatula in a patient's mouth and pharyngeal cavity. Further, the lumen of the respective laryngoscope spatulas is adapted to the diameter of the tube to be introduced. In order to indicate to the treating physician the maximum size of tube suited for the respective laryngoscope spatula, corresponding markings, stating for example the diameter in millimeters, may be provided on the laryngoscope spatulas, for example on their proximal ends.

What I claim is:

1. A laryngoscope, in particular for introducing a tube into a trachea of a patient, comprising:

a handle; and a laryngoscope spatula connected to said handle, said laryngoscope spatula having a longitudinal direction, and, further being configured, at least in part, as a tubular hollow body having a proximal end and a distal end, wherein said tubular hollow body comprises a lateral longitudinal opening extending from said distal end to said proximal end, and wherein said laryngoscope spatula comprises at its distal end a substantially flat tip adjacent to said distal end of said tubular hollow body, said tip having a distal end which is in transverse direction substantially straight, wherein a cross-sectional area of said laryngoscope spatula decreases in a proximal area of said tubular hollow body.

2. The laryngoscope of claim 1, wherein said laryngoscope spatula is approximately C-shaped in cross sections.

3. The laryngoscope of claim 1, wherein said lateral longitudinal opening has an opening angle, viewed in cross-section, in the range of approximately 180° to approximately 90°.

4. The laryngoscope of claim 1, wherein said tip is, in longitudinal direction, slightly curved or straight.

5. The laryngoscope of claim 1, wherein said tip is the distal end of said laryngoscope spatula.

6. The laryngoscope of claim 1, wherein said tip exhibits a thicker portion in a bead form.

7. The laryngoscope of claim 1, wherein a light pipe, having an output end which opens into a lumen of said laryngoscope spatula, is guided along said laryngoscope spatula.

8. The laryngoscope of claim 1, wherein said proximal end of said laryngoscope spatula comprises a mounting section for locking said handle on said laryngoscope spatula.

9. The laryngoscope of claim 1, wherein an insufflation channel is arranged on said laryngoscope spatula.

10. A laryngoscope, in particular for introducing a tube into a trachea of a patient, comprising:

a handle; and a laryngoscope spatula connected to said handle, said laryngoscope spatula having a longitudinal direction, and, further being configured, at least in part, as a tubular hollow body having a proximal end and a distal end, wherein said tubular hollow body comprises a lateral longitudinal opening extending from said distal end to said proximal end, and wherein said laryngoscope spatula comprises at its distal end a substantially flat tip adjacent to said distal end of said tubular hollow body, said tip having a distal end which is in transverse direction substantially straight, and wherein said lateral longitudinal opening of said tubular hollow body widens toward said proximal end of said tubular hollow body.

11. The laryngoscope of claim 10, wherein said laryngoscope spatula is approximately C-shaped in cross sections.

12. The laryngoscope of claim 10, wherein said lateral longitudinal opening has an opening angle, viewed in cross-section, in the range of approximately 180° to approximately 90°.

13. The laryngoscope of claim 10, wherein said tip is, in longitudinal direction, slightly curved or straight.

14. The laryngoscope of claim 10, wherein said tip is the distal end of said laryngoscope spatula.

15. The laryngoscope of claim 10, wherein said tip exhibits a thicker portion in a bead form.

16. The laryngoscope of claim 10, wherein a light pipe, having an output end which opens into a lumen of said laryngoscope spatula, is guided along said laryngoscope spatula.

17. The laryngoscope of claim 10, wherein said proximal end of said laryngoscope spatula comprises a mounting section for locking said handle on said laryngoscope spatula.

18. The laryngoscope of claim 10, wherein an insufflation channel is arranged on said laryngoscope spatula.

* * * * *